United States Patent
Kiyose et al.

(10) Patent No.: US 10,085,720 B2
(45) Date of Patent: Oct. 2, 2018

(54) ULTRASONIC DEVICE, METHOD FOR PRODUCING ULTRASONIC DEVICE, ULTRASONIC PROBE, ULTRASONIC MEASUREMENT APPARATUS, AND ELECTRONIC DEVICE

(71) Applicant: SEIKO EPSON CORPORATION, Tokyo (JP)

(72) Inventors: Kanechika Kiyose, Nagano (JP); Nobuaki Hashimoto, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 650 days.

(21) Appl. No.: 14/839,056

(22) Filed: Aug. 28, 2015

(65) Prior Publication Data

US 2016/0058417 A1 Mar. 3, 2016

(30) Foreign Application Priority Data

Aug. 29, 2014 (JP) .................. 2014-175113

(51) Int. Cl.

| A61B 8/00 | (2006.01) |
|---|---|
| A61B 8/08 | (2006.01) |
| G01N 29/24 | (2006.01) |
| G01N 29/34 | (2006.01) |
| G01S 15/89 | (2006.01) |
| G01S 7/52 | (2006.01) |
| B06B 1/06 | (2006.01) |

(52) U.S. Cl.
CPC .......... *A61B 8/4494* (2013.01); *A61B 8/4427* (2013.01); *A61B 8/4444* (2013.01); *B06B 1/067* (2013.01); *B06B 1/0629* (2013.01); *G01S 7/52079* (2013.01); *G01S 15/8925* (2013.01)

(58) Field of Classification Search
CPC ............. G01S 15/8925; G01S 7/52079; A61B 8/4494; A61B 8/4444; A61B 8/4427; B06B 1/0629; B06B 1/067
See application file for complete search history.

(56) References Cited

U.S. PATENT DOCUMENTS

| 9,079,220 | B2 * | 7/2015 | Nakamura | ............ B06B 1/0622 |
|---|---|---|---|---|
| 9,099,635 | B2 * | 8/2015 | Nakamura | ............ B06B 1/0629 |
| 9,184,370 | B2 * | 11/2015 | Kano | ................. H01L 41/0475 |
| 9,197,331 | B2 * | 11/2015 | Nishiwaki | .............. H04B 11/00 |
| 9,513,263 | B2 * | 12/2016 | Endo | .................... G01N 29/262 |
| 9,554,775 | B2 * | 1/2017 | Nakamura | ............ B06B 1/0622 |
| 9,592,534 | B2 * | 3/2017 | Nakamura | ............ B06B 1/0629 |

(Continued)

FOREIGN PATENT DOCUMENTS

| JP | 2010-539442 A | 12/2010 |
|---|---|---|
| JP | 2012-135622 A | 7/2012 |

(Continued)

*Primary Examiner* — Daniel Pihulic

(57) ABSTRACT

An ultrasonic device includes an element substrate and a wiring substrate. The element substrate includes an ultrasonic element and an element interconnect terminal connected to the ultrasonic element. The wiring substrate includes a wiring terminal and an opening portion that defines an opening extending through the wiring substrate. The element interconnect terminal and the wiring terminal are connected so as to oppose each other. The opening portion encloses the ultrasonic element in plan view as seen from a thickness direction of the wiring substrate.

15 Claims, 9 Drawing Sheets

(56) References Cited

U.S. PATENT DOCUMENTS

| | | | |
|---|---|---|---|
| 9,692,524 B2* | 6/2017 | Nishiwaki | H04B 11/00 |
| 2010/0036257 A1 | 2/2010 | Sano et al. | |
| 2010/0277040 A1 | 11/2010 | Klee et al. | |
| 2013/0223184 A1* | 8/2013 | Takahashi | B06B 1/0622 |
| | | | 367/7 |
| 2013/0223192 A1* | 8/2013 | Nishiwaki | H04B 11/00 |
| | | | 367/135 |
| 2013/0258802 A1* | 10/2013 | Nakamura | B06B 1/0207 |
| | | | 367/7 |
| 2014/0104989 A1* | 4/2014 | Matsuda | G01N 29/0654 |
| | | | 367/138 |
| 2014/0116148 A1* | 5/2014 | Endo | G01H 11/08 |
| | | | 73/661 |
| 2014/0241112 A1* | 8/2014 | Kano | H01L 41/0475 |
| | | | 367/7 |
| 2015/0027228 A1* | 1/2015 | Endo | G01N 29/262 |
| | | | 73/641 |
| 2016/0038120 A1* | 2/2016 | Kano | H01L 41/0475 |
| | | | 600/459 |
| 2016/0056901 A1* | 2/2016 | Nishiwaki | H04B 11/00 |
| | | | 367/13 |
| 2016/0058415 A1* | 3/2016 | Nakamura | A61B 8/4477 |
| | | | 600/459 |
| 2016/0058417 A1* | 3/2016 | Kiyose | G01S 15/8925 |
| | | | 600/472 |
| 2017/0020484 A1* | 1/2017 | Kiyose | A61B 8/4494 |
| 2017/0031024 A1* | 2/2017 | Kiyose | G01S 15/8915 |
| 2018/0091235 A1* | 3/2018 | Matsuda | H04B 11/00 |

FOREIGN PATENT DOCUMENTS

| | | | |
|---|---|---|---|
| JP | 2013-144063 A | | 7/2013 |
| JP | 2013144063 A | * | 7/2013 |
| JP | 2013-211604 A | | 10/2013 |
| JP | 2014-146884 A | | 8/2014 |

* cited by examiner

ULTRASONIC DEVICE, METHOD FOR PRODUCING ULTRASONIC DEVICE, ULTRASONIC PROBE, ULTRASONIC MEASUREMENT APPARATUS, AND ELECTRONIC DEVICE

CROSS-REFERENCE TO RELATED APPLICATIONS

This application claims priority to Japanese Patent Application No. 2014-175113 filed on Aug. 29, 2014. The entire disclosure of Japanese Patent Application No. 2014-175113 is hereby incorporated herein by reference.

BACKGROUND

Technical Field

The present invention relates to an ultrasonic device, a method for producing an ultrasonic device, and an ultrasonic probe, an ultrasonic measurement apparatus, and an electronic device that use the ultrasonic device.

Related Art

As an ultrasonic device, there is disclosed an ultrasonic transducer element chip including ultrasonic transducer elements provided in openings arranged in an array pattern on a first surface of a substrate, and a reinforcing member fixed on a second surface of the substrate that is opposite to the first surface, wherein the reinforcing member includes linear groove parts that provide communication between the openings and the external space. There is also disclosed an ultrasonic diagnostic apparatus including an ultrasonic probe on which the ultrasonic transducer element chip is mounted.

In the ultrasonic diagnostic device, the ultrasonic transducer element chip is electrically connected via a flexible printed circuit substrate (hereinafter abbreviated as "FPC") to a transmitting and receiving circuit for emitting ultrasonic waves from the ultrasonic transducer element and receiving reflected waves of the ultrasonic waves by the ultrasonic transducer element.

JP A-2013-211604 is an example of related art.

SUMMARY

However, the use of a relay substrate such as an FPC to electrically connect the wiring substrate including at least a part of the transmitting and receiving circuit and the ultrasonic transducer element chip causes a voltage drop in electric signals exchanged between the transmitting and receiving circuit and the ultrasonic transducer elements due to the wiring resistance of the relay substrate itself or the connection resistance in the connection to the relay substrate, for example. Also, there is the problem that noise tends to be introduced into the relay substrate from the outside.

The invention has been made in order to solve at least some of the above-described problems, and can be implemented in the form of the following embodiments or application examples.

According one aspect of the invention, an ultrasonic device includes an element substrate and a wiring substrate. The element substrate includes an ultrasonic element and an element interconnect terminal connected to the ultrasonic element. The wiring substrate includes a wiring terminal and an opening portion that defines an opening extending through the wiring substrate. The element interconnect terminal and the wiring terminal are connected so as to oppose each other. The opening portion encloses the ultrasonic element in plan view as seen from a thickness direction of the wiring substrate.

According to the aspect of the invention, the ultrasonic device further includes an acoustic matching layer and an acoustic lens that are stacked in order in the opening of the opening portion from a side of the element substrate.

According to the aspect of the invention, the ultrasonic device further includes a sealing member packed into a gap between the opening portion and the acoustic lens.

According to the aspect of the invention, the ultrasonic device further includes an acoustic matching layer that fills the opening of the opening portion and is in contact with the element substrate, and an acoustic lens attached to the wiring substrate so as to be in contact with the acoustic matching layer at a position overlapping the opening portion.

According to the aspect of the invention, a surface of the acoustic lens that is in contact with the acoustic matching layer is larger than the opening of the opening portion.

According to another aspect of the invention, a method for producing an ultrasonic device includes providing an element substrate including an ultrasonic element and an element interconnect terminal connected to the ultrasonic element, and a wiring substrate including a wiring terminal and an opening portion that defines an opening extending through the wiring substrate, and mounting the element substrate to the wiring substrate such that the ultrasonic element and the opening of the opening portion oppose each other, and the element interconnect terminal and the wiring terminal are connected.

According to the aspect of the invention, the method further includes forming an acoustic matching layer on a plane of an acoustic lens, the acoustic lens including a convex lens surface and the plane opposing the lens surface, and incorporating, into the opening of the opening portion of the wiring substrate, the acoustic lens on which the acoustic matching layer is formed such that the acoustic matching layer is in contact with the element substrate.

According to the aspect of the invention, the method further includes packing a sealing member into a gap between the opening portion and the acoustic lens.

According to the aspect of the invention, the method further includes packing an acoustic matching layer forming member so as to fill the opening of the opening portion of the wiring substrate to which the element substrate is mounted, removing the acoustic matching layer forming member extruded from an opposite surface opposite to a surface of the wiring substrate to which the wiring terminal is provided, and disposing an acoustic lens on the opposite surface of the wiring substrate at a position overlapping the opening portion.

According to the aspect of the invention, the method further includes disposing a sealing member at an outer peripheral portion of the acoustic lens and fixing the acoustic lens to the opposite surface of the wiring substrate.

According to another aspect of the invention, an ultrasonic probe includes the ultrasonic device according to the aspect of the invention as mentioned above.

According to another aspect of the invention, an ultrasonic probe includes the ultrasonic device produced by the method according to the aspect of the invention as mentioned above.

According to another aspect of the invention, an ultrasonic measurement apparatus includes the ultrasonic probe according to the aspect of the invention as mentioned above, a processing portion configured to form an image by processing an output from the ultrasonic device of the ultrasonic probe, and a display portion configured to display the image.

According to another aspect of the invention, an electronic device includes the ultrasonic device according to the aspect of the invention as mentioned above.

According to another aspect of the invention, an electronic device includes the ultrasonic device produced by the method according to the aspect of the invention as mentioned above.

BRIEF DESCRIPTION OF THE DRAWINGS

Referring now to the attached drawings which form a part of this original disclosure.

DETAILED DESCRIPTION OF EXEMPLARY EMBODIMENTS

Hereinafter, embodiments of the invention will be described with reference to the drawings. Note that the drawings used are shown in a larger or smaller size as needed so that a portion to be described is recognizable.

First Embodiment

Electronic Device

Figure 1:
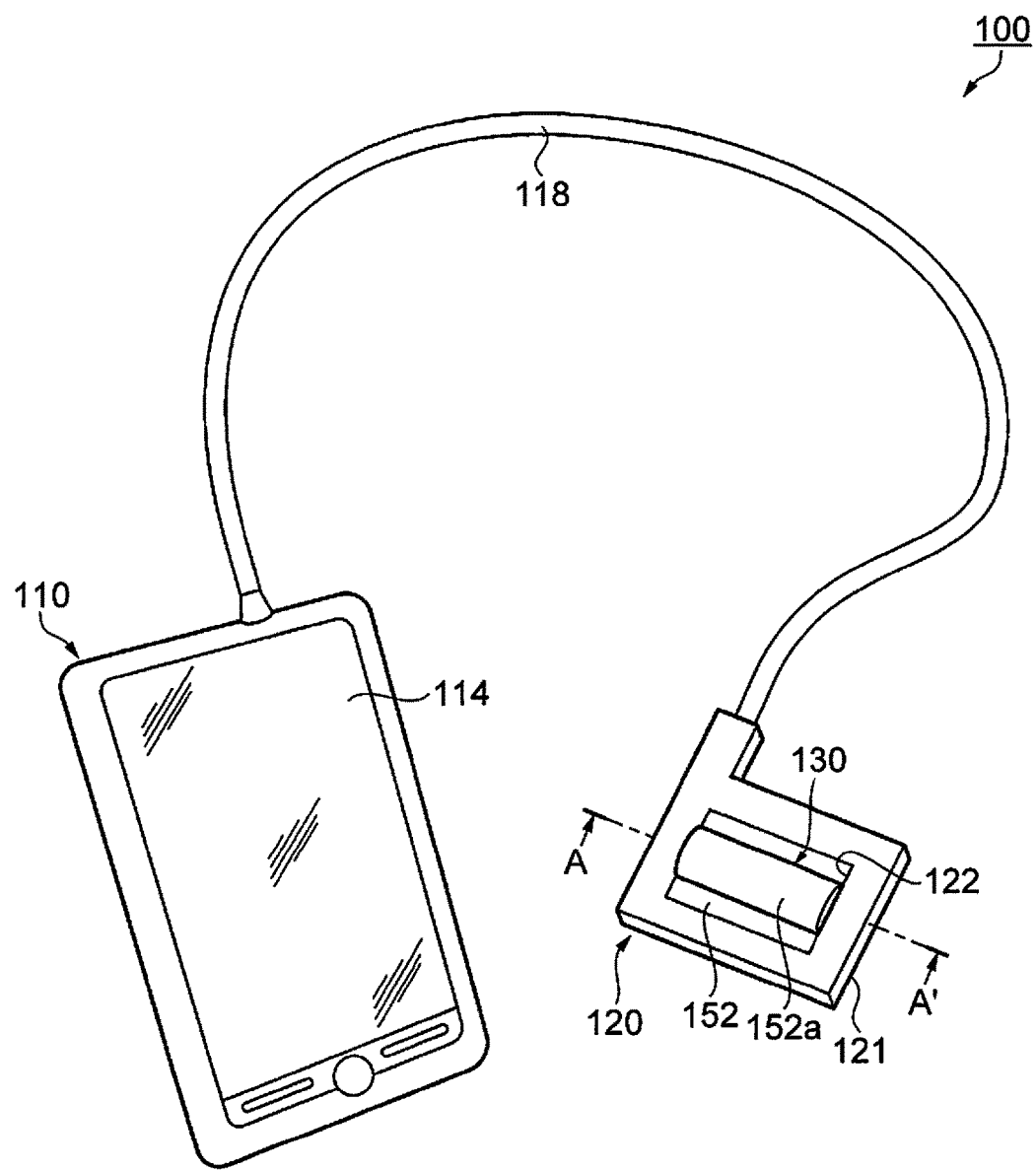
FIG. 1 is a perspective view showing a configuration of an ultrasonic measurement apparatus.
Figure 2:
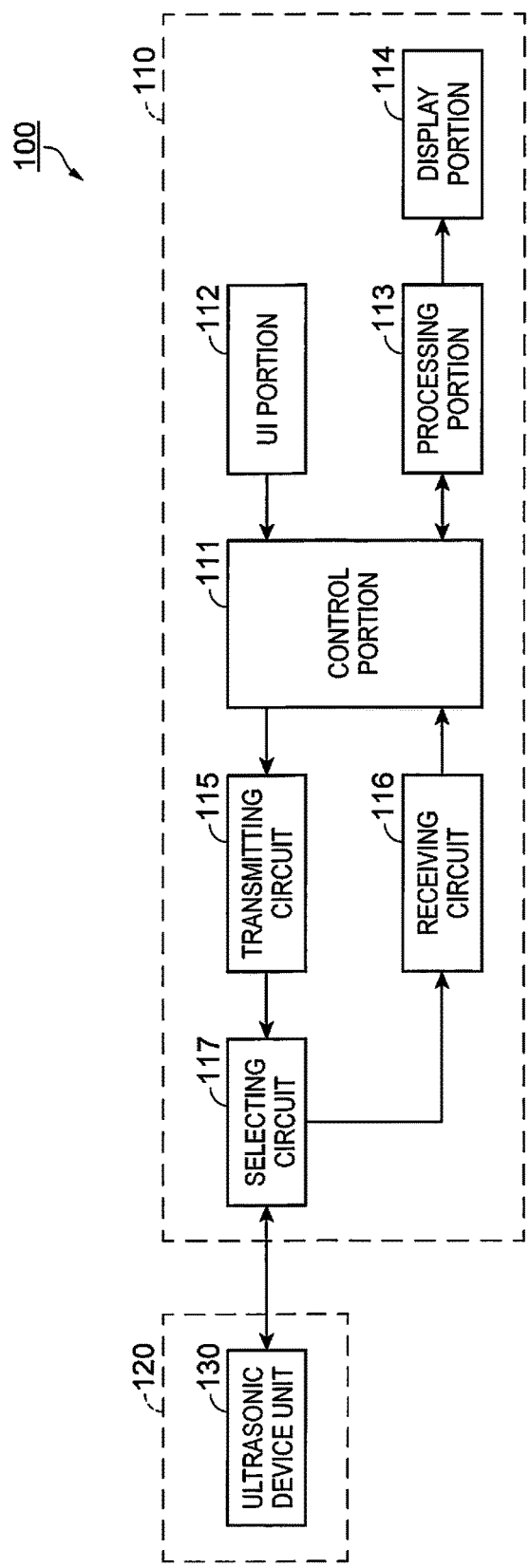
FIG. 2 is a block diagram showing an electrical configuration of the ultrasonic measurement apparatus.

First, as an example of an electronic device according to the present embodiment, an ultrasonic measurement apparatus will be described with reference to FIGS. 1 and 2. FIG. 1 is a perspective view showing a configuration of the ultrasonic measurement apparatus, and FIG. 2 is a block diagram showing an electrical configuration of the ultrasonic measurement apparatus.

As shown in FIG. 1, an ultrasonic measurement apparatus 100 as the electronic device according to the present embodiment includes an apparatus body 110 and an ultrasonic probe 120 electrically connected to the apparatus body 110 via a cable 118. The ultrasonic measurement apparatus 100 is an apparatus capable of putting the ultrasonic probe 120, for example, on a specific area of the human body as an object to be measured, receiving, by the ultrasonic probe 120, reflected waves (echo waves) generated as a result of the ultrasonic waves emitted from the ultrasonic probe 120 having been reflected inside the human body, and displaying the received information as an image in a display portion 114 of the apparatus body 110.

The apparatus body 110 is of tablet type, and contains various circuits (described in detail later) for driving the ultrasonic probe 120. In addition, touch-type input means (not shown) is incorporated into the display portion 114, and the operations associated with operation icons, buttons, or the like displayed in the display portion 114 can be performed by the user touching the various operation icons, buttons or the like.

The ultrasonic probe 120 includes an ultrasonic device unit 130 as the ultrasonic device according to the present embodiment, and a housing (case) 121 in which the ultrasonic device unit 130 is incorporated. The ultrasonic device unit 130 includes an acoustic lens 152 that is provided so as to protrude from a window hole 122 of the housing (case) 121, comes into contact with the object to be measured to transmit ultrasonic waves thereto, and guides the reflected waves of the ultrasonic waves to the inside of the ultrasonic probe 120. The acoustic lens 152 has a lens surface 152a that is cylindrical (which refers to a part of a curved surface that is a side surface of a cylinder). The lens surface 152a is a portion that comes into contact with the object to be measured. Note that, in order for ultrasonic waves and reflected waves thereof to be efficiently transmitted and received, measurement using the ultrasonic probe 120 is performed by applying a gel containing moisture to, for example, a specific area of a human body, which is the object to be measured, before putting the acoustic lens 152 thereon.

As shown in FIG. 2, the ultrasonic measurement apparatus 100 includes the apparatus body 110 and the ultrasonic probe 120 containing the ultrasonic device unit 130. The apparatus body 110 includes a control portion 111, a user interface portion (UI portion) 112, a processing portion 113, a display portion 114, a transmitting circuit 115, a receiving circuit 116, and a selecting circuit 117. Each of the control portion 111 and the processing portion 113 includes a Central Processing Unit (CPU), an Application-Specific Integrated Circuit (ASIC), or the like.

The transmitting circuit 115 outputs a transmission signal serving as an electric signal for causing the ultrasonic device unit 130 to emit ultrasonic waves via the selecting circuit 117 during a transmission period. The frequency and the voltage amplitude of the transmission signal can be set by the control portion 111 via the UI portion 112.

The receiving circuit 116 receives a reception signal serving as an electric signal from the ultrasonic device unit 130 via the selecting circuit 117 during a reception period. In addition, the receiving circuit 116 performs reception processing such as amplification and A/D conversion (analog/digital conversion) of the received reception signal. The receiving circuit 116 can be configured, for example, by a low-noise amplifier, a voltage-controlled attenuator, a programmable gain amplifier, a low-pass filter, an A/D converter, and the like.

The control portion 111 controls the transmitting circuit 115 and the receiving circuit 116. Specifically, the control portion 111 controls the processing of generating and outputting the transmission signal for the transmitting circuit 115, and controls the settings of the frequency and the gain of the reception signal for the receiving circuit 116.

The selecting circuit 117 outputs a selected transmission signal based on the control performed by the control portion 111.

The UI portion 112 includes the above-described touch-type input means, and is connected to the control portion 111. The UI portion 112 outputs a necessary instruction (command) to the control portion 111 based on an operation (e.g., an operation of the touch-type input means) performed by the user.

The processing portion 113 receives detection data from the receiving circuit 116, and performs, for example, necessary image processing and generates display image data.

The display portion 114 is, for example, a liquid crystal display connected to the processing portion 113, and displays the display image data output from the processing portion 113.

The ultrasonic measurement apparatus 100 according to the present embodiment is a portable ultrasonic measurement apparatus that includes an ultrasonic probe 120 on which a small and thin ultrasonic device unit 130 is mounted, and is driven by a power supply (not shown in FIGS. 1 and 2) contained in the apparatus body 110. Note that the power supply is not limited to being contained in the apparatus body 110, and may be a member separate from the apparatus body 110. Alternatively, it is possible to adopt a configuration in which power is supplied from the outside through a power cord.

Ultrasonic Device

Figure 3:
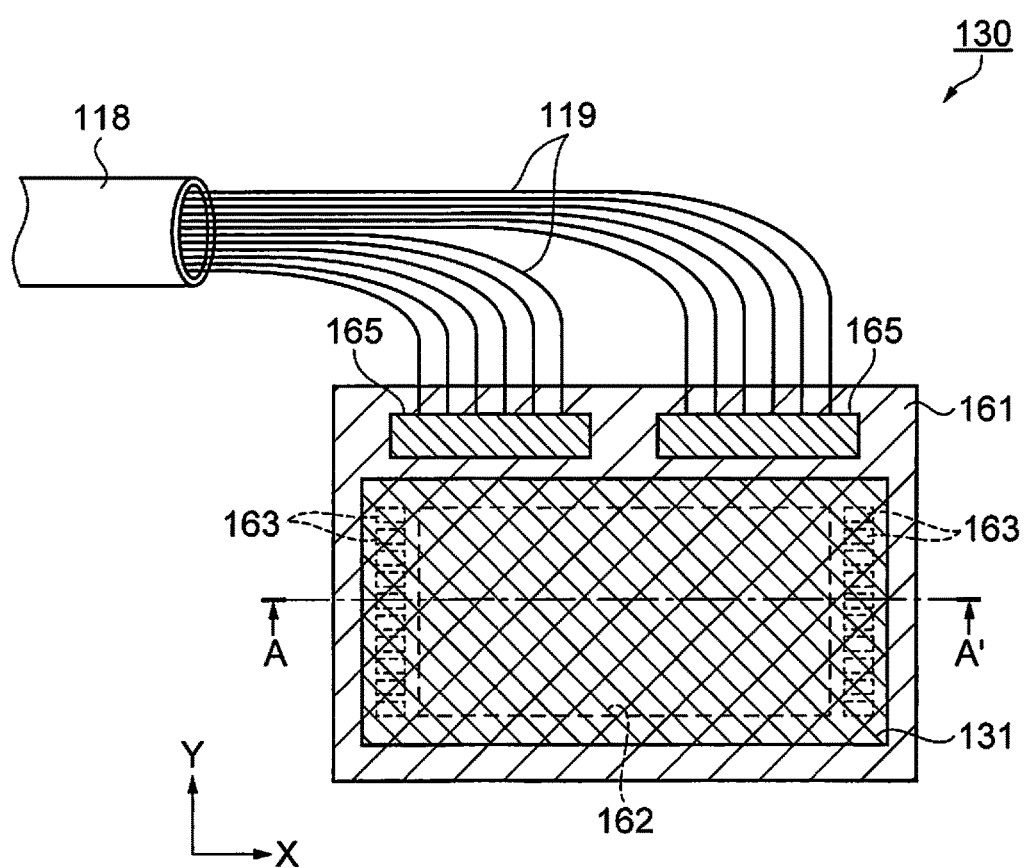
FIG. 3 is a schematic plan view showing a configuration of an ultrasonic device unit according to a first embodiment.
Figure 4A:
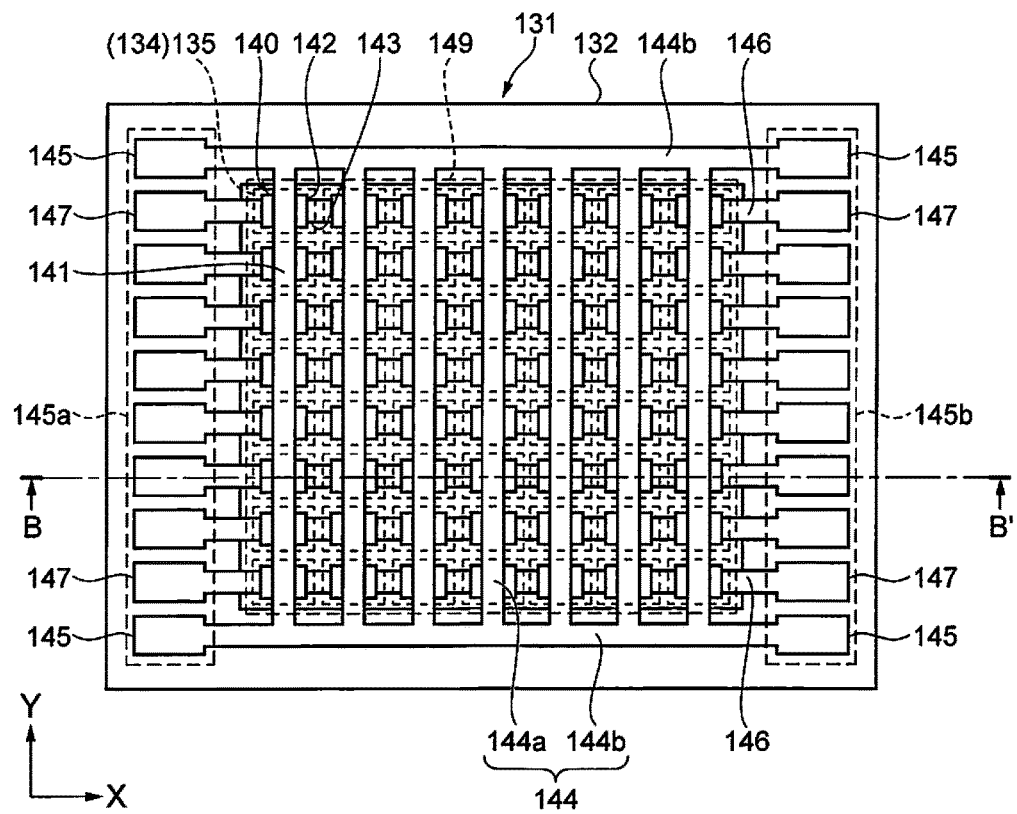
FIG. 4A is a schematic plan view showing a configuration of an element substrate.
Figure 4B:
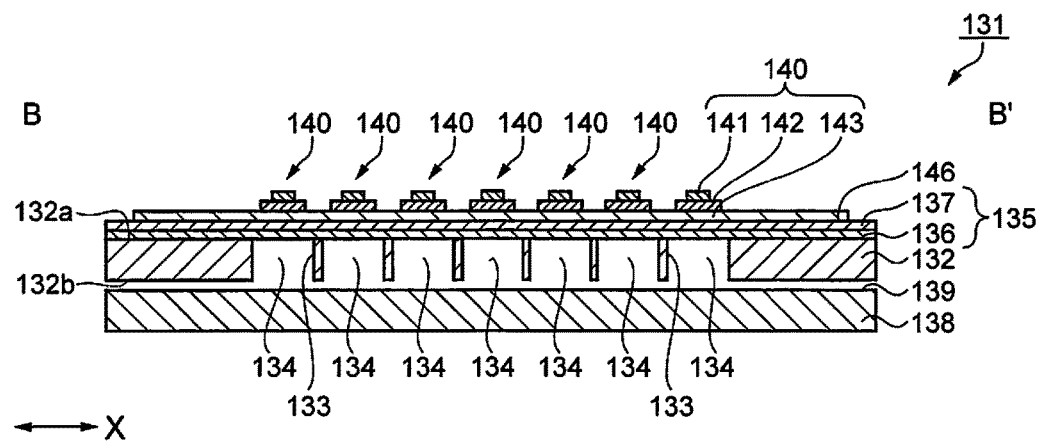
FIG. 4B is a schematic cross-sectional view showing a structure of the element substrate, taken along the lines B-B' in FIG. 4A.
Figure 5:
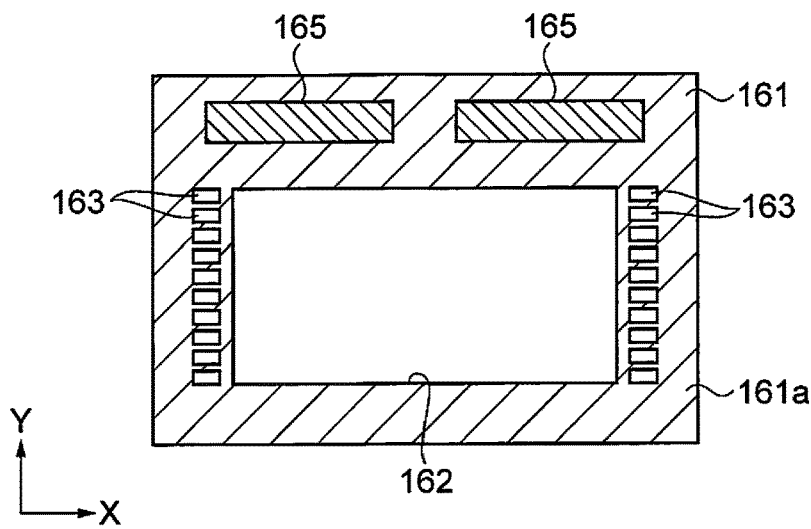
FIG. 5 is a schematic plan view showing a configuration of a wiring substrate.
Figure 6:
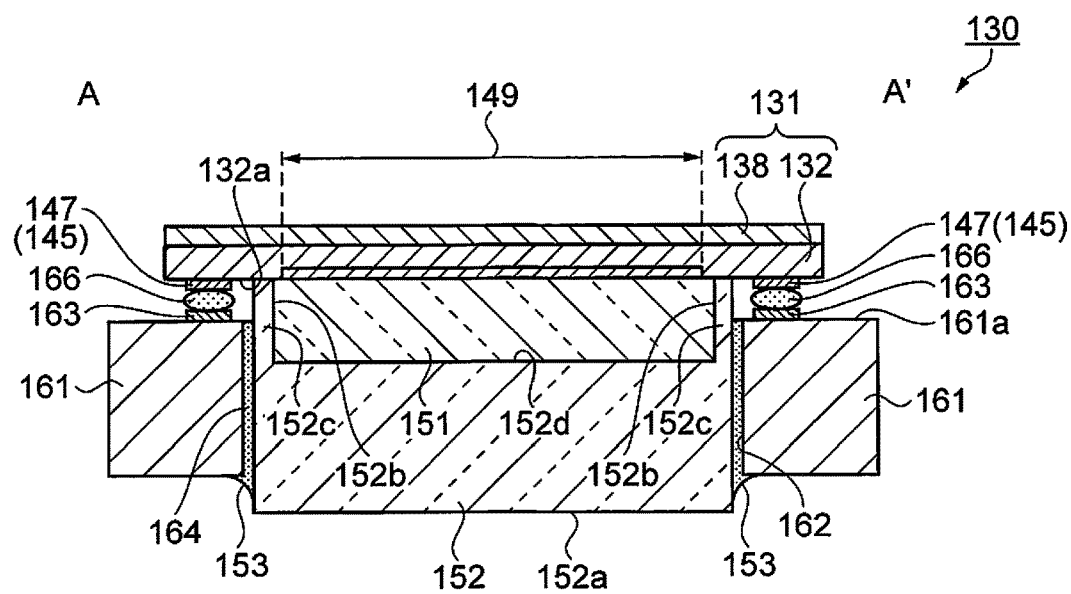
FIG. 6 is a schematic cross-sectional view showing a structure of the ultrasonic device unit according to the first embodiment.

Next, the ultrasonic device unit 130 serving as an ultrasonic device according to the present embodiment will be described with reference to FIGS. 3 to 6. FIG. 3 is a schematic plan view showing a configuration of the ultrasonic device unit. FIG. 4A is a schematic plan view showing a configuration of an element substrate. FIG. 4B is a schematic cross-sectional view showing a structure of the element substrate, taken along the line B-B' in FIG. 4A. FIG. 5 is a schematic plan view showing a configuration of a wiring substrate. FIG. 6 is a schematic cross-sectional view showing a structure of the ultrasonic device unit. Note that FIG. 6 is a schematic cross-sectional view taken along the line A-A' in FIG. 1 or 3.

As shown in FIG. 3, the ultrasonic device unit 130 includes an element substrate 131 and a wiring substrate 161. The element substrate 131 is provided with ultrasonic elements. The wiring substrate 161 is provided with a plurality of wiring terminals 163 and two connectors 165. The element substrate 131 is surface-mounted on a mounting surface, of the wiring substrate 161, on which the wiring terminals 163 are provided. Wires 119 of the cable 118 are connected to the connectors 165.

The element substrate 131 and the wiring substrate 161 each have a square outside shape, and the following description will be given taking the length direction of the element substrate 131 and the wiring substrate 161 as the X direction, and the width direction, which is orthogonal to the length direction, as the Y direction.

As shown in FIG. 4A, the element substrate 131 includes piezoelectric elements 140 disposed along the X direction and the Y direction. In the present embodiment, a total of 56 piezoelectric elements 140, namely, 7 piezoelectric elements 140 at equal intervals in the X direction and 8 piezoelectric elements 140 at equal intervals in the Y direction are disposed. In other words, assuming that rows extend in the X direction and columns extend in the Y direction, the piezoelectric elements 140 are arranged in 8 rows and 7 columns. The region in which the plurality of piezoelectric elements 140 are disposed is referred to as an "element region 149". Note that the number of the piezoelectric elements 140 arranged in the element region 149 is not limited to the aforementioned number. Also, the arrangement of the piezoelectric elements 140 in the element region 149 is not limited to an arrangement in which they are arranged at equal intervals in each of the X direction and the Y direction. For example, it is possible to adopt an arrangement in which they are alternately offset in the X direction (rows) or in the Y direction (columns).

As shown in FIGS. 4A and 4B, the piezoelectric elements 140 each include an upper electrode 141, a lower electrode 143, and a piezoelectric film 142 sandwiched between these electrodes. The piezoelectric film 142 is, for example, a lead zirconate titanate (PZT) film.

The element substrate 131 includes an upper electrode interconnect 144 including first interconnect portions 144a disposed so as to span eight piezoelectric films 142 aligned in the Y direction, and a pair of second interconnect portions 144b connected to opposite ends of seven first interconnect portions 144a and extending in the X direction. The element substrate 131 also includes lower electrode interconnects 146 disposed so as to span seven piezoelectric films 142 aligned in the X direction and provided under the piezoelectric films 142. In other words, the first interconnect portions 144a provided on a column-by-column basis each function as the upper electrode 141 of the eight piezoelectric elements 140 aligned in the Y direction. Also, the lower electrode interconnects 146 provided on a row-by-row basis each function as the lower electrode 143 of the seven piezoelectric elements 140 aligned in the X direction. The upper electrode interconnects 144 are formed using iridium (Ir), for example. The lower electrode interconnects 146 are formed using, for example, titanium (Ti), iridium (Ir), and platinum (Pt), or may be formed by stacking layers of these metals.

Element interconnect terminals 145 are provided at opposite ends of the pair of second interconnect portions 144b extending in the X direction. Likewise, element interconnect terminals 147 are provided at opposite ends of the lower electrode interconnect 146 extending in the X direction. At the left end of the element substrate 131 in the X direction, a terminal portion 145a including two element interconnect terminals 145 and eight element interconnect terminals 147 disposed between the two element interconnect terminal 145 at equal intervals in the Y direction is provided. Likewise, at the right end of the element substrate 131 in the X direction, a terminal portion 145b including two element interconnect terminals 145 and eight element interconnect terminals 147 disposed between the two element interconnect terminals 145 at equal intervals in the Y direction is provided.

As shown in FIG. 4B, the element substrate 131 includes a substrate body 132 and a diaphragm 135 stacked on a first surface 132a of the substrate body 132. In the present embodiment, the diaphragm 135 includes a first dielectric film 136 and a second dielectric film 137 that are stacked in order on the first surface 132a. The first dielectric film 136 is a silicon oxide ($SiO_2$) film, for example, and the second dielectric film 137 is a zirconium oxide ($ZrO_2$) film, for example. The plurality of piezoelectric elements 140 are disposed on the second dielectric film 137 of the diaphragm 135.

As the substrate body 132, a semiconductor substrate of silicon or the like is used, for example. The thickness of the substrate body 132 is 0.15 mm, for example. In the substrate body 132, spaces 134 are formed so as to correspond to respective ones of the piezoelectric elements 140. Adjacent spaces 134 are partitioned by a wall 133. That is, the spaces 134 and the walls 133 corresponding to respective ones of the piezoelectric elements 140 disposed in the X direction and the Y direction in the element region 149 are formed in the substrate body 132, and the first surface 132a side of the spaces 134 is closed by the diaphragm 135. As shown in FIG. 4A, the size of the spaces 134 in plan view is larger than the size of the piezoelectric films 142.

A reinforcing plate 138 is provided on a second surface 132b of the substrate body 132 that is opposite to the first surface 132a. As the reinforcing plate 138, a metal plate made of an iron-nickel alloy, a silicon substrate, or the like can be used, for example. The material and the thickness of the reinforcing plate 138 affect the frequency characteristics of the ultrasonic device unit 130, and therefore, they are set based on the center frequency of the ultrasonic device unit 130. In the present embodiment, a 42 alloy (iron-nickel alloy) having a smaller coefficient of thermal expansion near room temperature than other metal materials is used as the reinforcing plate 138, and its thickness is 0.1 mm, for example. The reinforcing plate 138 is provided with grooves 139 for bringing seven spaces 134 adjacent in the X direction in the substrate body 132 into communication with the outside air. In other words, a plurality of the grooves 139 are provided in the reinforcing plate 138 on a row-by-row basis such that communication is provided between the seven spaces 134 provided in the substrate body 132 so as to correspond to respective ones of the seven piezoelectric elements 140 disposed on the diaphragm 135 in the X direction. Note that the grooves 139 are not limited to being provided on a row-by-row basis, and may be provided on a column-by-column basis, or may be provided on both a row-by-row basis and a column-by-column basis. Further, the means for bringing the spaces 134 into communication with the outside air is not limited to the grooves 139. For example, holes extending through the reinforcing plate 138 or a combination of grooves and holes may be used to bring the spaces 134 into communication with the outside air.

With such a configuration of the element substrate 131, the application of, for example, a square wave having a predetermined frequency between the upper electrode interconnect 144 and the lower electrode interconnect 146 enables the piezoelectric elements 140 to be driven on a row-by-row basis and/or a column-by-column basis to vibrate the diaphragm 135, thereby generating ultrasonic waves. Further, by the reflected waves (echo waves) of the ultrasonic waves vibrating the diaphragm 135, an electric signal having a predetermined frequency can be generated between the upper electrode 141 and the lower electrode 143 of each piezoelectric element 140.

The ultrasonic waves generated by the vibration of the diaphragm 135 are not only released to the piezoelectric element 140 side with respect to the substrate body 132, but also propagates to the reinforcing plate 138 side via the spaces 134 and are reflected by the reinforcing plate 138. The ultrasonic waves reflected by the reinforcing plate 138 are released from the piezoelectric element 140 side via the spaces 134 again. Accordingly, in order to prevent an attenuation of the ultrasonic waves directly released by the vibration of the diaphragm 135 and the ultrasonic waves reflected by the reinforcing plate 138 due to a phase shift therebetween, the acoustic distance of the spaces 134 is set to be an odd multiple of one fourth ($\lambda/4$) of the wavelength $\lambda$ of the ultrasonic waves. In other words, the thickness of the substrate body 132 and the thickness of the reinforcing plate 138 are set taking into consideration the wavelength $\lambda$ of the ultrasonic waves emitted from the ultrasonic elements each composed of a piezoelectric element 140 serving as an actuator (electromechanical transducing element) and the diaphragm 135.

Note that the piezoelectric element 140 also functions as an electromechanical transducing element that converts the energy (force) of the reflected waves received by the diaphragm 135 into an electric signal. Further, the element substrate 131 may have a configuration including the reinforcing plate 138 as in the present embodiment, or can have a configuration that does not include the reinforcing plate 138. In addition, the spaces 134 are not limited to air layers, and may be resin layers of silicone or the like, for example.

As shown in FIG. 5, the wiring substrate 161 on which the element substrate 131 is surface-mounted is a rigid glass epoxy wiring substrate, for example, and includes an opening portion 162 extending through the wiring substrate 161, and a plurality of wiring terminals 163 and two connectors 165 that are provided on a mounting surface 161a. The opening portion 162 includes an interior surface (inner wall) of the wiring substrate 161, which defines an opening extending through the wiring substrate 161. The shape of the opening portion 162 is quadrangular. The size (shape and area) of the opening portion 162 is set so as not to inhibit the release of ultrasonic waves emitted from the element substrate 131 or not to inhibit the reflected waves of the ultrasonic waves from reaching the element substrate 131. Specifically, the size (shape and area) of the opening portion 162 is preferably the same as the size enclosing the element region 149 of the element substrate 131, or the size (shape and area) of the opening portion 162 is slightly larger than the size (area) of the element region 149. Note that the shape and the area of the element region 149 can be defined by the outer edge of the region occupied by the plurality of spaces 134 formed so as to correspond to respective ones of the plurality of piezoelectric elements 140 (see FIG. 4A).

The plurality of wiring terminals 163 are disposed so as to sandwich the opening portion 162 in the X direction, and are also disposed along the edges of the opening portion 162 in the Y direction. The plurality of wiring terminals 163 are disposed at equal intervals in the Y direction so as to correspond to the two element interconnect terminals 145 and the eight element interconnect terminals 147 of each of the terminal portions 145a and 145b of the element substrate 131 (see FIG. 4A).

As shown in FIG. 6, the ultrasonic device unit 130 includes the element substrate 131, the wiring substrate 161, an acoustic matching layer 151, and an acoustic lens 152. The element substrate 131 is surface-mounted (face-down mounted) to the mounting surface 161a of the wiring substrate 161. Specifically, the element substrate 131 and the wiring substrate 161 are disposed so as to oppose each other such that the element region 149 and the opening of the opening portion 162 face each other, and each element interconnect terminal 147 (145) and each wiring terminal 163 that are disposed so as to oppose each other are bonded via a bonding member 166. Consequently, the plurality of piezoelectric elements 140 provided on the element substrate 131 are electrically connected to the wiring substrate 161. The bonding member 166 may be, for example, a bump of gold, solder or the like, or may be a thermoplastic, anisotropic conductive film or anisotropic conductive adhesive.

The acoustic lens 152 is inserted into the opening of the opening portion 162 of the wiring substrate 161. As described above, the acoustic lens 152 has the cylindrical lens surface 152a and a recessed portion 152b provided on the opposite side of the lens surface 152a. The recessed portion 152b includes a supporting portion 152c and a plane 152d. An acoustic matching layer forming member is packed into the recessed portion 152b, thus forming the acoustic matching layer 151. The acoustic lens 152 is inserted into the opening of the opening portion 162 such that the supporting portion 152c is in contact with a portion of the element substrate 131 other than the element region 149 and the acoustic matching layer 151 is in contact at least with the element region 149. Then, a sealing member 153 is packed so as to fill a gap 164 between the side surface of the acoustic lens 152 and the inner wall of the opening portion 162. Consequently, the acoustic lens 152 is fixed to the wiring substrate 161. As the sealing member 153, a thermosetting epoxy resin having high moisture resistance performance and high adhesion performance is used, for example.

The acoustic lens 152 having the lens surface 152a and the recessed portion 152b is formed by packing and solidifying a transparent silicone resin, for example, into a mold. The acoustic matching layer 151 can also be formed by using a transparent silicone resin, for example. By forming the acoustic matching layer 151 with a member similar to that of the acoustic lens 152, it is possible to ensure the adhesion and the bonding of the acoustic matching layer 151 to the acoustic lens 152.

The acoustic matching layer 151 and the acoustic lens 152 are provided for efficiently transmitting ultrasonic waves generated in the element substrate 131, for example, to a human body, which is an object to be measured, and efficiently transmitting the reflected waves of the ultrasonic waves reflected from the human body to the element substrate 131. The propagation efficiency, or in other words, the acoustic impedance, of the ultrasonic waves and their reflected waves in the acoustic matching layer 151 and the acoustic lens 152 is set taking into consideration the acoustic impedances of the ultrasonic elements (including the piezoelectric elements 140 and the diaphragm 135) in the element substrate 131, and, for example, the human body serving as an object to be measured.

In the above-described ultrasonic measurement apparatus 100, the ultrasonic waves used for measurement have a frequency between 1 MHz and 30 MHz. The velocity of sound is known to vary depending on the object to which ultrasonic waves are transmitted and the temperature thereof. For example, when the object to be measured is a human body, it is assumed that the sound velocity of the ultrasonic waves used for measurement is 1530 m/s (second) (35° C.), which is a sound velocity in water, since the human body as a medium has properties close to water. When the acoustic impedance is represented as "Z", the acoustic impedance Z can be expressed by the product of the density ρ of the medium and the sound velocity C (Expression (1)).

$$Z = \rho \times C \quad (1)$$

Accordingly, when the density ρ of water is 1000 kg/m$^3$ and the sound velocity is 1530 m/s, the acoustic impedance Z of water, or in other words, the human body, is 1.5×10$^6$ kg/(m$^2$·s). This value is called 1.5 Mrayls (mega rayleigh).

The frequency of the ultrasonic waves emitted from the ultrasonic elements of the element substrate 131 according to the present embodiment is approximately 7.5 MHz, and the acoustic impedance is approximately 1 Mrayl. Accordingly, a value between 1 Mrayl and 1.5 Mrayls is set for the acoustic matching layer 151 and the acoustic lens 152. From the viewpoint of efficient transmission and reception of ultrasonic waves, it is preferable that the acoustic matching layer 151 has an acoustic impedance close to that of the ultrasonic elements and the acoustic lens 152 has an acoustic impedance close to that of the human body. The acoustic impedance of the acoustic matching layer 151 in the present embodiment is 1.2 Mrayls, for example, and the acoustic impedance of the acoustic lens 152 is 1.5 Mrayls. For the acoustic matching layer 151, it is necessary to consider the acoustic impedance as described above, and also to consider the thickness. When the thickness is large, ultrasonic waves tend to be attenuated while they propagate through the acoustic matching layer 151. Therefore, the acoustic matching layer 151 is preferably as thin as possible. The thickness of the acoustic matching layer 151 according to the present embodiment is approximately 0.1 mm. The thickness of the wiring substrate 161 in which the acoustic matching layer 151 and the acoustic lens 152 are housed in the opening portion 162 is approximately 0.5 mm. Note that the acoustic matching layer 151 is not limited to a single layer as in the present embodiment, and may have a multi-layer structure having varied acoustic impedances.

Method for Producing Ultrasonic Device

Next, a method for producing an ultrasonic device unit as a method for producing an ultrasonic device according to the present embodiment will be described with reference to FIGS. 7A to 7C and 8A to 8D. FIGS. 7A to 7C and FIGS. 8A to 8D are schematic cross-sectional views showing the method for producing an ultrasonic device unit.

The method for producing the ultrasonic device unit 130 according to the present embodiment includes providing the element substrate 131 and the wiring substrate 161 (step S1), mounting the element substrate 131 to the wiring substrate 161 (step S2), forming the acoustic matching layer 151 on the acoustic lens 152 (step S3), incorporating the acoustic lens 152 into the wiring substrate 161 (step S4), and packing the sealing member 153 into the gap between the opening portion 162 and the acoustic lens 152 (step S5). In the following, the method will be described in further details with reference to FIGS. 7A to 7C and 8A to 8D.

Figure 7A:
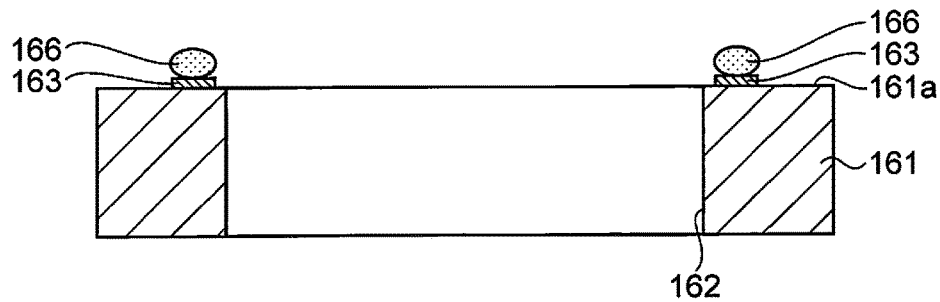
FIGS. 7A to 7C are schematic cross-sectional views showing a method for producing the ultrasonic device unit according to the first embodiment.

In step S1, the element substrate 131 on which piezoelectric elements 140 and the upper electrode interconnect 144 and the lower electrode interconnect 146 connected to the piezoelectric elements 140 are formed is provided. In addition, the wiring substrate 161 on which at least the opening portion 162 and the wiring terminals 163 are formed is provided. Then, as shown in FIG. 7A, the bonding member 166 is disposed on each wiring terminal 163 of the wiring substrate 161. In the present embodiment, an anisotropic conductive adhesive is used as the bonding member 166, and is applied to the wiring terminal 163. Examples of the method of application of the anisotropic conductive adhesive include printing and dispensing. Due to the use of the anisotropic conductive adhesive, adjacent wiring terminals 163 will not be short-circuited by the anisotropic conductive adhesive even if the adhesive is applied over the plurality of wiring terminals 163. Note that such placement of the bonding members 166 may be performed in the next step S2. Then, the method proceeds to step S2.

Figure 7B:
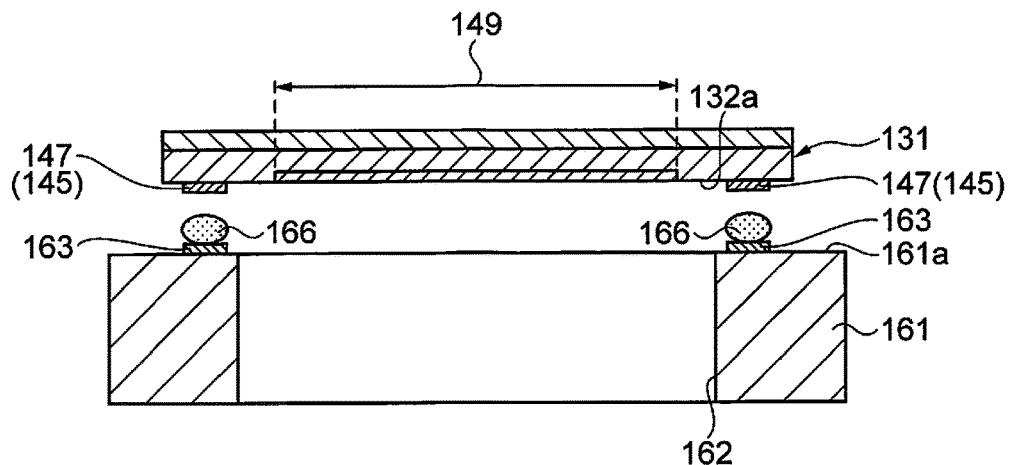
Figure 7C:
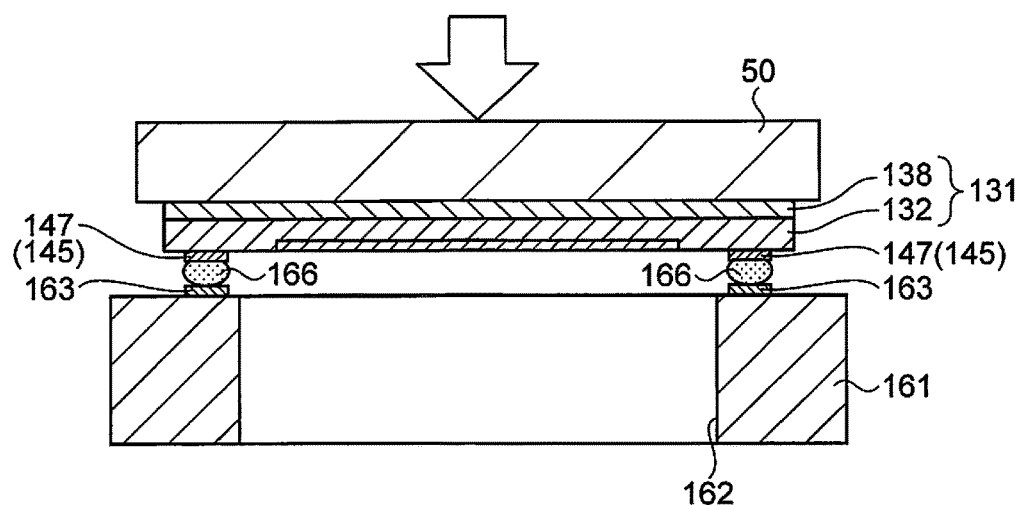

In step S2, as shown in FIG. 7B, the element substrate 131 and the wiring substrate 161 are positioned and disposed such that the element region 149 and the opening of the opening portion 162 face each other and each element interconnect terminal 147 (145) and each wiring terminal 163 on which the bonding member 166 is disposed oppose each other. Examples of the method of positioning and disposing the element substrate 131 and the wiring substrate 161 so as to oppose each other in this manner include a method in which the element interconnect terminal 147 (145) and the wiring terminal 163 are each recognized by image recognition by using an image-capturing unit such as a camera for the element substrate 131 and the wiring substrate 161 that are disposed at their respective different reference positions, and the element substrate 131 and the wiring substrate 161 are positioned and disposed so as to oppose each other by image processing by moving one of them relative to the other. Alternatively, the element substrate 131 and the wiring substrate 161 may be positioned and disposed so as to oppose each other by capturing an image of the element substrate 131 from a side of the opening of the opening portion 162 by using the opening of the opening portion 162 of the wiring substrate 161. Then, as shown in FIG. 7C, a pressure-bonding tool 50 is abutted against the reinforcing plate 138 of the element substrate 131 to press the element substrate 131 against the wiring substrate 161. At this time, the pressure-bonding tool 50 is heated by a heater or the like such that heat is conducted to the bonding member 166. The element substrate 131 is thermo-compressed to the wiring substrate 161 at a predetermined temperature for a predetermined time, and thereby, the element interconnect terminal 147 (145) and the wiring terminal 163 are bonded via the bonding member 166.

Figure 8A:
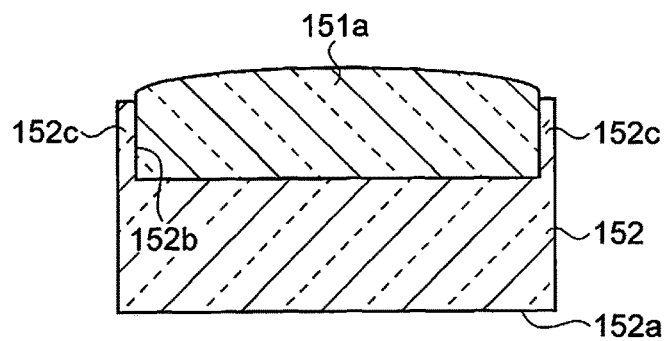
FIGS. 8A to 8D are schematic cross-sectional views showing the method for producing the ultrasonic device unit according to the first embodiment.
Figure 8B:
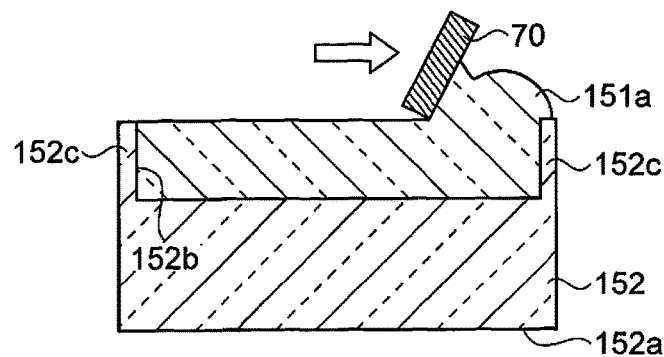
Figure 8C:
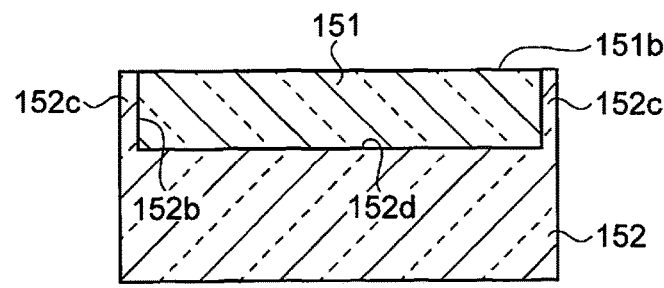

In step S3, first, an acoustic matching layer forming member 151a is packed into the recessed portion 152b of the acoustic lens 152, as shown in FIG. 8A. Next, a squeegee 70 is moved using the supporting portion 152c as a guide (guiding portion), and thereby, any excess acoustic matching layer forming member 151a extruded from the supporting portion 152c is scraped off with the squeegee 70. Consequently, an acoustic matching layer 151 is formed in which a surface 151b opposing the plane 152d of the recessed portion 152b is substantially flat, as shown in FIG. 8C. In other words, the acoustic matching layer 151 having a stable thickness with little variations is formed. Then, the method proceeds to step S4. Note that step S3 may not necessarily be performed after step S2, as long as it is performed prior to step S4.

Figure 8D:
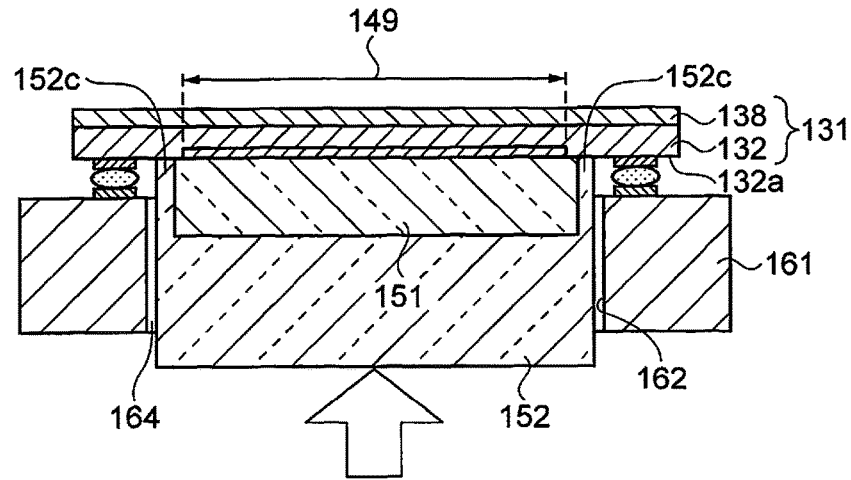

In step S4, as shown in FIG. 8D, the acoustic lens 152 on which the acoustic matching layer 151 is formed is inserted into the opening of the opening portion 162 of the wiring substrate 161. By inserting the acoustic lens 152 such that the supporting portion 152c thereof is abutted against the element substrate 131, the acoustic matching layer 151 and the element region 149 are disposed in contact with each other. Then, the method proceeds to step S5.

In step S5, the sealing member 153 is packed into the gap 164 (see FIGS. 6 and 8D) that has been formed between the side surface of the acoustic lens 152 and the inner wall of the opening portion 162 as a result of insertion of the acoustic lens 152 into the opening of the opening portion 162 of the wiring substrate 161, and the sealing member 153 is then solidified. Consequently, the acoustic lens 152 is fixed to the wiring substrate 161, thus completing the ultrasonic device unit 10 (see FIG. 6). Note that the sealing member 153 may also be packed into the gap between the first surface 132a of the element substrate 131 and the mounting surface 161a.

Further, the connectors 165 may be mounted before the element substrate 131 is surface-mounted to the wiring substrate 161, or may be mounted after the element substrate 131 has been surface-mounted to the wiring substrate 161.

According to the first embodiment, the following effects can be achieved.

(1) With the ultrasonic device unit 130 and the method for producing the same, the element substrate 131 is surface-mounted (face-down mounted) to the wiring substrate 161, and it is therefore possible to provide and produce an ultrasonic device unit 130 that is less affected by an attenuation in electric signals exchanged between the element substrate 131 and the wiring substrate 161 resulting from the wiring resistance or the connection resistance of a relay substrate such as an FPC, or by noise from the outside, has high connection reliability and is thin, as compared with a case where the relay substrate is used to connect the element interconnect terminals 145 and 147 of the element substrate 131 and the wiring terminal 163 of the wiring substrate 161.

(2) As the wiring substrate 161, it is possible to use a single-sided substrate in which the wiring terminal 163 and a routing wire can be disposed on the mounting surface 161a and an electronic component such as the connector 165 can be mounted on the mounting surface 161a. Therefore, it is possible to achieve a lower cost as compared with a case where a double-sided substrate or a multi-layer substrate is used.

(3) The ultrasonic device unit 130 includes the acoustic matching layer 151 and the acoustic lens 152. Further, the acoustic matching layer 151 is formed so as to fill the recessed portion 152b of the acoustic lens 152. Then, the acoustic lens 152 is inserted into the opening of the opening portion 162 of the wiring substrate 161 such that the acoustic matching layer 151 is in contact with the element region 149 of the element substrate 131, and is fixed with the sealing member 153. Accordingly, it is possible to provide and produce a thin ultrasonic device unit 130 capable of efficiently transmitting ultrasonic waves emitted from the element substrate 131, for example, to a human body, which is an object to be measured, and efficiently transmitting reflected waves of the ultrasonic waves from the human body to the element substrate 131.

(4) The sealing member 153 is packed into the gap 164 created as a result of insertion of the acoustic lens 152 into the opening of the opening portion 162 of the wiring substrate 161, and thereby, the wiring substrate 161 and the acoustic lens 152 are fixed. This can prevent the entry of moisture or the like from the gap 164, making is possible to prevent the degeneration of the acoustic matching layer 151 due to the influence of moisture, or prevent the destabilization of the bonding between the element interconnect terminal 147 (145) and the wiring terminal 163 via the bonding member 166.

(5) Since the ultrasonic probe 120 includes the above-described ultrasonic device unit 130, it is possible to achieve the ultrasonic probe 120 that has high connection reliability and is thin.

(6) Since the ultrasonic measurement apparatus 100 includes the above-described ultrasonic probe 120, it is possible to provide the ultrasonic measurement apparatus 100 that has high connection reliability and excellent portability.

Second Embodiment

Ultrasonic Device

Figure 9:
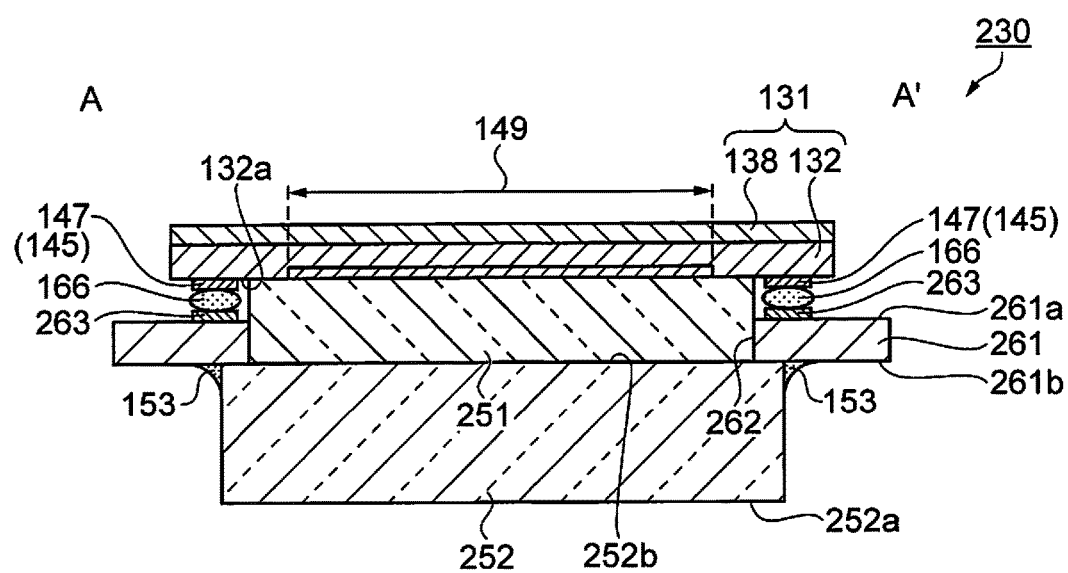
FIG. 9 is a schematic cross-sectional view showing a structure of an ultrasonic device unit according to a second embodiment.

Next, an ultrasonic device unit as an ultrasonic device according to a second embodiment will be described with reference to FIG. 9. FIG. 9 is a schematic cross-sectional view showing a structure of the ultrasonic device unit according to the second embodiment. The ultrasonic device unit according to the second embodiment is different from the ultrasonic device unit 130 according to the first embodiment in the configurations of the wiring substrate, the acoustic matching layer, and the acoustic lens. The components that are the same as those of the first embodiment are denoted by the same reference numerals, and the detailed description thereof has been omitted. Note that FIG. 9 is a schematic cross-sectional view that can be compared with the ultrasonic device unit 130 according to the first embodiment shown in FIG. 6.

As shown in FIG. 9, an ultrasonic device unit 230 according to the present embodiment includes the element substrate 131, a wiring substrate 261, an acoustic matching layer 251, and an acoustic lens 252. The wiring substrate 261 is provided with an opening portion 262 including an interior surface (inner wall) of the wiring substrate 261, which defines an opening and extends through the wiring substrate 261, and the opening of the opening portion 262 extends through the wiring substrate 261 and is open in the same size as or a size larger than the size of the element region 149. A plurality of wiring terminals 263 are provided on a mounting surface 261a of the wiring substrate 261 along the edge portion of the opening portion 262. The element substrate 131 is surface-mounted (face-down mounted) to the mounting surface 261a of the wiring substrate 261. Specifically, the element substrate 131 and the wiring substrate 261 are disposed so as to oppose each other such that the element region 149 and the opening of the opening portion 262 face each other, and each element interconnect terminal 147 (145) and each wiring terminal 263 disposed so as to oppose each other are bonded via the bonding member 166. Consequently, the plurality of piezoelectric elements 140 provided on the element substrate 131 are electrically connected to the wiring substrate 261. As described in the first embodiment, the bonding member 166 may be, for example, a bump of gold, solder or the like, or may be a thermoplastic, anisotropic conductive film or anisotropic conductive adhesive. In the present embodiment, a thermoplastic, anisotropic conductive adhesive is used as the bonding member 166.

The acoustic matching layer 251 is formed so as to fill the opening of the opening portion 262 of the wiring substrate 261 and to be in contact with the element region 149 of the element substrate 131 that is surface-mounted to the wiring substrate 261.

The acoustic lens 252 includes a cylindrical lens surface 252a and a flat surface 252b opposing the lens surface 252a. The size (area) of the surface 252b is larger than the size (area) of the opening of the opening portion 262. Also, the acoustic lens 252 is disposed on a surface 261b of the wiring substrate 261 that is opposite to the mounting surface 261a such that the surface 252b is in contact with the acoustic matching layer 251. Furthermore, a sealing member 153 is disposed at the outer peripheral portion of the acoustic lens 252, and the acoustic lens 252 is fixed to the surface 261b of the wiring substrate 261 with the sealing member 153.

As in the first embodiment, the acoustic matching layer 251 is formed by using a transparent silicone resin, for example. The acoustic lens 252 is also formed by molding, for example, a transparent silicone resin using a mold, as in the first embodiment. The acoustic impedances of the acoustic matching layer 251 and the acoustic lens 252 are set so as to have a value between 1 Mrayl and 1.5 Mrayls. The acoustic impedance of the acoustic matching layer 251 is 1.2 Mrayls, for example, and the acoustic impedance of the acoustic lens 252 is 1.5 Mrayls, for example.

Method for Producing Ultrasonic Device

Next, a method for producing an ultrasonic device unit as a method for producing an ultrasonic device according to a second embodiment will be described with reference to FIGS. 10A to 10D. FIGS. 10A to 10D are schematic cross-sectional views showing the method for producing an ultrasonic device unit according to the second embodiment.

The method for producing an ultrasonic device unit 230 according to the present embodiment includes providing the element substrate 131 and the wiring substrate 261 (step S11), mounting the element substrate 131 to the wiring substrate 261 (step S12), forming an acoustic matching layer 251 (step S13), disposing an acoustic lens 252 on the wiring substrate 261 (step S14), and fixing the acoustic lens 252 to the wiring substrate 261 (step S15). Hereinafter, the method will be described in further detail with reference to FIGS. 10A to 10D. Note that the details of step S11 are the same as those of step S1 in the first embodiment, and therefore, the detailed description thereof has been omitted.

Figure 10A:
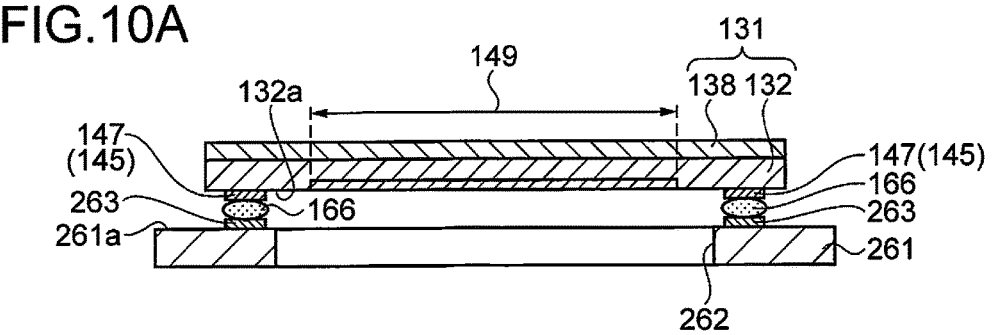
FIGS. 10A to 10D are schematic cross-sectional views showing a method for producing the ultrasonic device unit according to the second embodiment.

In step S12, as shown in FIG. 10A, the element substrate 131 and the wiring substrate 261 are positioned and disposed such that the element region 149 of the element substrate 131 and the opening of the opening portion 262 face each other and each element interconnect terminal 147 (145) and each wiring terminal 263 on which the bonding member 166 is disposed oppose each other. Then, the element substrate 131 are thermo-compressed to the wiring substrate 261 at a predetermined temperature for a predetermined time, and thereby, the element interconnect terminal 147 (145) and the wiring terminal 263 are bonded via the bonding member 166. Then, the method proceeds to step S13.

Figure 10B:
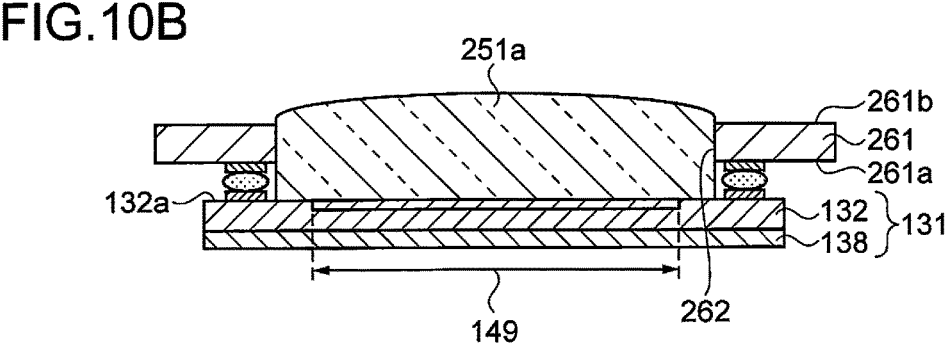
Figure 10C:
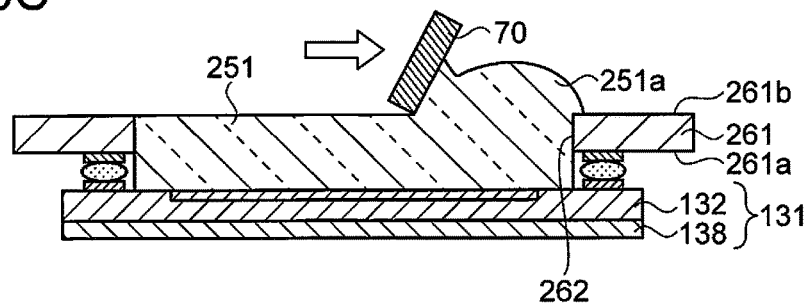

In step S13, as shown in FIG. 10B, the wiring substrate 261 to which the element substrate 131 is surface-mounted is turned upside down, and an acoustic matching layer forming member 251a is packed so as to fill the opening of the opening portion 262. Next, any excess acoustic matching layer forming member 251a extruded from the surface 261b that is opposite to the mounting surface 261a of the wiring substrate 261 is removed. Specifically, as shown in FIG. 10C, the squeegee 70 is moved while being put on the surface 261b of the wiring substrate 261, and thereby, any excess acoustic matching layer forming member 251a extruded from the surface 261b is scraped off with the squeegee 70. Consequently, an acoustic matching layer 251 is formed whose surface exposed in the opening of the opening portion 262 of the wiring substrate 261 is substantially flat. Then, the method proceeds to step S14.

Figure 10D:
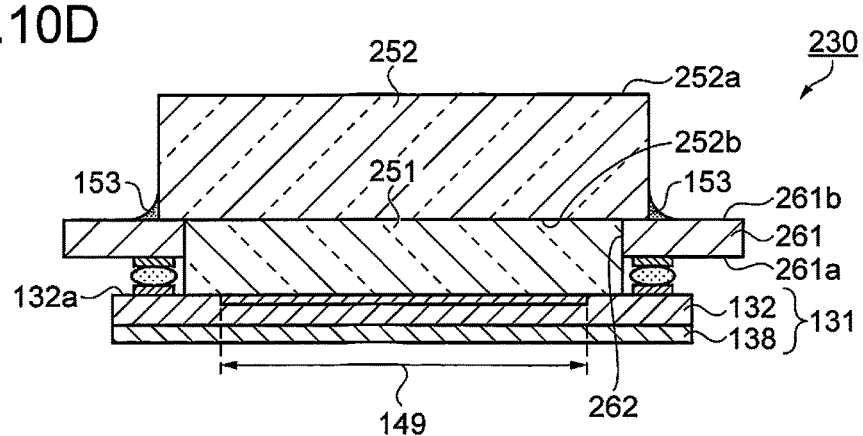

In step S14, as shown in FIG. 10D, the acoustic lens 252 is disposed on the surface 261b of the wiring substrate 261 such that the surface 252b of the acoustic lens 252 overlaps the opening portion 262 and the surface 252b is in contact with the acoustic matching layer 251. Subsequently, the sealing member 153 is disposed at the outer peripheral portion of the acoustic lens 252 and then solidified, thereby fixing the acoustic lens 252 to the surface 261b of the wiring substrate 261. This completes the ultrasonic device unit 230.

According to the above-described second embodiment, it is possible to achieve the following effects, in addition to the effects (1), (2), (5), and (6) of the above-described first embodiment.

(7) With the above-described ultrasonic device unit 230 and the method for producing the same, the acoustic matching layer 251 is formed so as to fill the opening of the opening portion 262 of the wiring substrate 261, and any excess acoustic matching layer forming member 251a extruded from the wiring substrate 261 is removed. Accordingly, the thickness of the acoustic matching layer 251 can be controlled by adjusting the thickness of the wiring substrate 261. The molding of the acoustic lens 252 is facilitated as compared with a case where the recessed portion 152b in which the acoustic matching layer 151 is formed is provided on the acoustic lens 152 as in the first embodiment. Further, since the acoustic lens 252 does not have a protruding portion, breakage of the acoustic lens 252 due to an impact caused by a fall or the like, and cracking of the acoustic lens 252 do not easily occur. That is, it is possible to provide the ultrasonic device unit 230 having excellent impact resistance.

(8) The opening of the opening portion 262 of the wiring substrate 261 is filled with the acoustic matching layer 251, and is closed by the flat surface 252b of the acoustic lens 252. In addition, the outer peripheral portion of the acoustic lens 252 is sealed with the sealing member 153, and therefore, moisture or the like does not easily enter the opening of the opening portion 262 as compared with the first embodiment. That is, it is possible to more reliably prevent the degeneration of the acoustic matching layer 251 due to moisture or the like, or the destabilization of the bonding state as a result of moisture or the like entering into the bonded portion between the element substrate 131 and the wiring substrate 261.

Note that in the second embodiment, when the thickness of the acoustic matching layer 251 is changed, the thickness of the wiring substrate 261 needs to be changed at the same time. In contrast, the first embodiment is advantageous in that the thickness of the wiring substrate 161 does not need to be changed even if the thickness of the acoustic matching layer 151 is changed, and therefore, the wiring substrate 161 can be used as a common component. In other words, the second embodiment is advantageous in that the acoustic lens 252 can be used as a common component.

It should be appreciated that the invention is not limited to the embodiments described above, and may be appropriately modified within the range that does not depart from the gist or spirit of the invention, which can be read from the appended claims and the overall specification, and that an ultrasonic device and a method for producing the ultrasonic device with such modifications, as well as an ultrasonic probe and an ultrasonic measurement apparatus (electronic device) to which the ultrasonic device is applied are also encompassed within the technical scope of the invention. Various modifications other than the above-described embodiments are possible. In the following, examples of the modifications will be described.

Modification 1

The ultrasonic device is not limited to a unit configuration including an acoustic matching layer and an acoustic lens. It is possible to adopt a configuration in which the element substrate is surface-mounted to the wiring substrate without providing an acoustic matching layer and an acoustic lens, or a configuration in which the acoustic matching layer is provided on the wiring substrate to which the element substrate is surface-mounted.

Modification 2

The piezoelectric element 140 constituting the ultrasonic elements is not limited to a structure in which the piezoelectric film 142 is sandwiched between the upper electrode 141 and the lower electrode 143. For example, it is possible to adopt a structure in which the first electrode and the second electrode are spaced so as to oppose each other on the piezoelectric film 142.

Modification 3

The electronic device to which the ultrasonic device of the embodiments is applied is not limited to the ultrasonic measurement apparatus 100. For example, the ultrasonic device of the embodiments can be applied to an ultrasonic in-liquid measuring instrument, an ultrasonic aerial measuring instrument, and the like.

An ultrasonic device according to the example includes an element substrate including an ultrasonic element and an element wiring terminal connected to the ultrasonic element on a first surface; and a wiring substrate including an opening portion extending therethrough in the thickness direction and being open in a size enclosing a region in which the ultrasonic element is disposed and a wiring terminal provided on a mounting surface other than the opening portion. The ultrasonic element on the first surface and the opening portion are disposed so as to oppose each other, and the element wiring terminal and the wiring terminal are connected so as to oppose each other.

According to the example, the element substrate is face-down mounted to the wiring substrate, and it is therefore possible to provide an ultrasonic device that is less affected by the attenuation in electric signals resulting from the wiring resistance or the connection resistance of the relay substrate and the noise from the outside, has high connection reliability, and is thin as compared with a case where the relay substrate is used to electrically connect the element substrate and the wiring substrate.

Preferably, the ultrasonic device according to the example includes an acoustic matching layer and an acoustic lens that are stacked in order in the opening portion from the element substrate side.

With this configuration, by interposing the acoustic lens and the acoustic matching layer between the ultrasonic element and, for example, a human body, which is an object of interest having an acoustic impedance different from that of the ultrasonic element, ultrasonic waves emitted from the ultrasonic element can be efficiently applied to the human body. Further, ultrasonic waves that are reflected, for example, from the human body, which is an object of interest to which the ultrasonic waves are applied, can be efficiently received by the ultrasonic element.

Preferably, the ultrasonic device according to the example includes a sealing member packed into a gap between the opening portion and the acoustic lens.

With this configuration, moisture or the like can be prevented from entering from the gap between the opening portion and the acoustic lens by the sealing member. That is, it is possible, with the sealing member, to prevent a reduction or loss of the properties and function of the acoustic matching layer and the element substrate due to moisture or the like.

The ultrasonic device according to the example may include an acoustic matching layer that fills the opening portion and is in contact with the element substrate; and an acoustic lens attached to the wiring substrate so as to be in contact with the acoustic matching layer at a position overlapping the opening portion.

With this configuration, the thickness of the acoustic matching layer can be accurately ensured by adjusting the thickness of the wiring substrate having the opening portion. Since the thickness of the acoustic matching layer affects the acoustic impedance, it is possible to achieve an ultrasonic device capable of transmitting ultrasonic waves to the object of interest in a more efficient manner.

In the ultrasonic device according to the example, it is preferable that a surface of the acoustic lens that is in contact with the acoustic matching layer is larger than the opening portion.

With this configuration, the opening portion of the wiring substrate is closed by the acoustic lens, and moisture or the like does not readily enter from the opening portion. Accordingly, it is possible to achieve an ultrasonic device having high connection reliability.

A method for producing an ultrasonic device according to the example includes: providing an element substrate including an ultrasonic element and an element wiring terminal connected to the ultrasonic element on a first surface, and a wiring substrate including an opening portion extending therethrough in the thickness direction and being open in a size enclosing a region in which the ultrasonic element is disposed and a wiring terminal provided on a mounting surface other than the opening portion; and mounting the element substrate to the wiring substrate such that the ultrasonic element on the first surface and the opening portion oppose each other, and connecting the element wiring terminal and the wiring terminal.

According to the example, the element substrate is face-down mounted to the wiring substrate, and it is therefore possible to produce an ultrasonic device that is less affected by the attenuation in signals resulting from the connection resistance of the relay substrata and the noise from the outside, has high connection reliability, and is thin, as compared with a case where the relay substrate is used to electrically connect the element substrate and the wiring substrate.

Preferably, the method for producing an ultrasonic device according to the example includes: forming an acoustic matching layer on a plane of an acoustic lens, the acoustic lens including a convex lens surface and the plane opposing the lens surface; and incorporating, into the opening portion of the wiring substrate, the acoustic lens on which the acoustic matching layer is formed such that the acoustic matching layer is in contact with the element substrate.

With this method, by interposing the acoustic lens and the acoustic matching layer between the ultrasonic element and, for example, a human body, which is an object of interest having an acoustic impedance different from that of the ultrasonic element, ultrasonic waves emitted from the ultrasonic element can be efficiently applied to the human body. In addition, it is possible to produce an ultrasonic device capable of efficiently receiving ultrasonic waves that are reflected, for example, from the human body, which is an object of interest to which the ultrasonic waves are applied, by the ultrasonic element.

Preferably, the method for producing an ultrasonic device according to the example includes packing a sealing member into a gap between the opening portion and the acoustic lens.

With this method, moisture or the like can be prevented from entering into the gap between the opening portion and the acoustic lens by the sealing member. That is, it is possible, with the sealing member, to prevent a reduction or loss of the properties or function of the acoustic matching layer and the element substrate due to moisture or the like, and produce an ultrasonic device having higher connection reliability.

The method for producing an ultrasonic device according to the example may include: packing an acoustic matching layer forming member so as to fill the opening portion of the wiring substrate to which the element substrate is mounted; removing the acoustic matching layer forming member extruded from a surface opposite to the mounting surface of the wiring substrate; and disposing an acoustic lens on the opposite surface of the wiring substrate at a position overlapping the opening portion.

With this method, the thickness of the acoustic matching layer can be accurately defined by the thickness of the wiring substrate having the opening portion by removing any acoustic matching layer forming member extruded from the wiring substrate. Since the thickness of the acoustic matching layer affects the acoustic impedance, it is possible to produce an ultrasonic device capable of transmitting ultrasonic waves to the object of interest in a more efficient manner.

Preferably, the method for producing an ultrasonic device according to the example includes disposing a sealing member at an outer peripheral portion of the acoustic lens and fixing the acoustic lens to the opposite surface of the wiring substrate.

With this method, it is possible to fix the acoustic lens such that no gap is formed between the wiring substrate and the acoustic lens, and prevent the entry of moisture or the like into the acoustic matching layer or the first surface of the element substrate from the outside. That is, it is possible to produce an ultrasonic device having higher connection reliability.

An ultrasonic probe according to the example includes the ultrasonic device according to the above-described example.

An ultrasonic probe according to the example includes an ultrasonic device produced by the method for producing an ultrasonic device according to the above-described example.

According to these examples, it is possible to provide an ultrasonic probe that is thinner and has higher connection reliability than in the past.

An ultrasonic measurement apparatus according to the example includes: the ultrasonic probe according to the above-described example, a processing portion that forms an image by processing an output from the ultrasonic device of the ultrasonic probe; and a display portion that displays the image.

According to the example, it is possible to put the ultrasonic probe on a specific area of, for example, a human body as an object to be measured, receive reflected waves of the ultrasonic waves emitted from the ultrasonic device by the ultrasonic device, and display the conditions inside the specific area as an image in the display portion, thus making it possible to provide an ultrasonic measurement apparatus having high connection reliability.

An electronic device according to the example includes the ultrasonic device according to the above-described example.

An electronic device according to the example includes an ultrasonic device produced by the method for producing an ultrasonic device according to the above-described example.

According to these examples, it is possible to provide an electronic device including an ultrasonic device that is thin and has high connection reliability.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An ultrasonic device comprising:
    an element substrate including an ultrasonic element and an element interconnect terminal connected to the ultrasonic element; and
    a wiring substrate including a wiring terminal and an opening portion that defines an opening extending through the wiring substrate,
    the element interconnect terminal and the wiring terminal being connected so as to oppose each other, and
    the opening portion enclosing the ultrasonic element in plan view as seen from a thickness direction of the wiring substrate.

2. The ultrasonic device according to claim 1, further comprising an acoustic matching layer and an acoustic lens that are stacked in order in the opening of the opening portion from a side of the element substrate.

3. The ultrasonic device according to claim 2, further comprising a sealing member packed into a gap between the opening portion and the acoustic lens.

4. The ultrasonic device according to claim 1, further comprising an acoustic matching layer that fills the opening of the opening portion and is in contact with the element substrate, and
    an acoustic lens attached to the wiring substrate so as to be in contact with the acoustic matching layer at a position overlapping the opening portion.

5. The ultrasonic device according to claim 4, wherein a surface of the acoustic lens that is in contact with the acoustic matching layer is larger than the opening of the opening portion.

6. A method for producing an ultrasonic device, the method comprising:
    providing an element substrate including an ultrasonic element and an element interconnect terminal connected to the ultrasonic element, and a wiring substrate including a wiring terminal and an opening portion that defines an opening extending through the wiring substrate; and
    mounting the element substrate to the wiring substrate such that the ultrasonic element and the opening of the opening portion oppose each other, and the element interconnect terminal and the wiring terminal are connected.

7. The method for producing the ultrasonic device according to claim 6, further comprising
    forming an acoustic matching layer on a plane of an acoustic lens, the acoustic lens including a convex lens surface and the plane opposing the lens surface, and
    incorporating, into the opening of the opening portion of the wiring substrate, the acoustic lens on which the acoustic matching layer is formed such that the acoustic matching layer is in contact with the element substrate.

8. The method for producing the ultrasonic device according to claim 7, further comprising packing a sealing member into a gap between the opening portion and the acoustic lens.

9. The method for producing the ultrasonic device according to claim 6, further comprising
    packing an acoustic matching layer forming member so as to fill the opening of the opening portion of the wiring substrate to which the element substrate is mounted,
    removing the acoustic matching layer forming member extruded from an opposite surface opposite to a surface of the wiring substrate to which the wiring terminal is provided, and
    disposing an acoustic lens on the opposite surface of the wiring substrate at a position overlapping the opening portion.

10. The method for producing the ultrasonic device according to claim 9, further comprising disposing a sealing member at an outer peripheral portion of the acoustic lens and fixing the acoustic lens to the opposite surface of the wiring substrate.

11. An ultrasonic probe comprising the ultrasonic device according to claim 1.

12. An ultrasonic probe comprising the ultrasonic device produced by the method according to claim 6.

13. An ultrasonic measurement apparatus comprising:
    the ultrasonic probe according to claim 11;
    a processing portion configured to form an image by processing an output from the ultrasonic device of the ultrasonic probe; and
    a display portion configured to display the image.

14. An electronic device comprising the ultrasonic device according to claim 1.

15. An electronic device comprising the ultrasonic device produced by the method according to claim 6.

* * * * *